(12) United States Patent
Lefebvre

(10) Patent No.: US 6,484,918 B1
(45) Date of Patent: Nov. 26, 2002

(54) STETHOSCOPE HOLDER

(76) Inventor: Gigi C. Lefebvre, 6471-90$^{th}$ Ave. N., Pinellas Park, FL (US) 33782

( * ) Notice: Subject to any disclaimer, the term of this patent is extended or adjusted under 35 U.S.C. 154(b) by 0 days.

(21) Appl. No.: 10/029,076

(22) Filed: Dec. 21, 2001

(51) Int. Cl.$^7$ ............................................. A45C 11/00
(52) U.S. Cl. ...................... 224/670; 181/131; 224/269; 224/678
(58) Field of Search .................. 224/670, 678, 224/269, 270; D24/134; D6/567; 181/131

(56) References Cited

U.S. PATENT DOCUMENTS

| | | | |
|---|---|---|---|
| 742,790 A | 10/1903 | Jones | |
| D229,514 S | 12/1973 | Einhorn | |
| 3,797,717 A | 3/1974 | Collins | |
| 5,171,087 A | 12/1992 | Green | |
| D375,161 S | * 10/1996 | Hart | D24/134 |
| 5,692,657 A | 12/1997 | Kilo et al. | |
| D425,353 S | 5/2000 | Foy | |
| 6,065,563 A | 5/2000 | Stowers | |
| D445,185 S | * 7/2001 | Najmi | D24/134 |
| 6,283,348 B1 | 9/2001 | Wang | |
| 6,419,133 B1 | * 7/2002 | Grose | 224/269 |

* cited by examiner

Primary Examiner—Stephen P. Garbe
Assistant Examiner—Maerena W. Brevard
(74) Attorney, Agent, or Firm—Larson & Larson, PA; James E. Larson

(57) ABSTRACT

Combined stethoscope integral housing and belt adapter for mounting a stethoscope on the belt of a care giver. The integral housing has a back wall and first and second side walls. The upper portion of each side wall contains an ear piece receptacle. A pair of front walls are spaced apart from each other to form a slot and spaced apart from the back wall to form an opening for a stethoscope chest piece. The belt adapter is hingedly attached to a back upper portion of the housing by an axially mounted rod.

6 Claims, 8 Drawing Sheets

STETHOSCOPE HOLDER

TECHNICAL FIELD

This invention relates to stethoscope holders. More particularly, it refers to a stethoscope holder generally mounted on the belt of a health provider and having a slotted front opening for receipt of a stethoscope chest piece as well as longitudinal bores for receipt of the stethoscope ear pieces.

BACKGROUND PRIOR ART

A stethoscope is an important medical instrument carried by most care givers at some time during their days' medical activities. Frequently, the stethoscope is stuck in a pocket of a medical coat where it occupies space needed frequently for other medical devices. Clip-on devices for carrying the stethoscope on a belt have been devised such as shown in U.S. Pat. No. Des 425,353. Unfortunately, the ear pieces on the stethoscope are not retained in a fixed position in this device and they have a tendency to flip out. Another prior art stethoscope holder is shown in U.S. Pat. No. 6,065,563, but this holder merely drapes the tubes from the stethoscope in a belt clip. This causes the chest piece and ear pieces to bounce when carried by a care giver. An improved stethoscope belt holder is needed which securely mounts the chest piece and ear pieces, but still permits ready access for use with patients by the care giver.

SUMMARY OF THE INVENTION

The belt mounted stethoscope holder of this invention provides ready access to the stethoscope by being mounted on the care giver's belt, but at the same time, is securely fastened out of the way and outside a care giver's pocket. The stethoscope holder is an integral housing with a combined belt adapter hingedly moving on a rod mounted on a top rear portion of the integral housing. The integral housing has a rear wall and a pair of side walls with ear piece receptacles mounted in a top portion of each side wall. A pair of front walls are spaced apart from each other to form a slot and spaced apart from the back wall to form an opening for receipt of a stethoscope chest piece. An opening at a bottom of the slot accommodates a stethoscope tube.

BRIEF DESCRIPTION OF THE DRAWINGS

The invention can be best understood by those having ordinary skill in the art by reference to the following detailed description when considered in conjunction with the accompanying drawings in which.

BEST MODE FOR CARRYING OUT THE INVENTION

Figure 1:
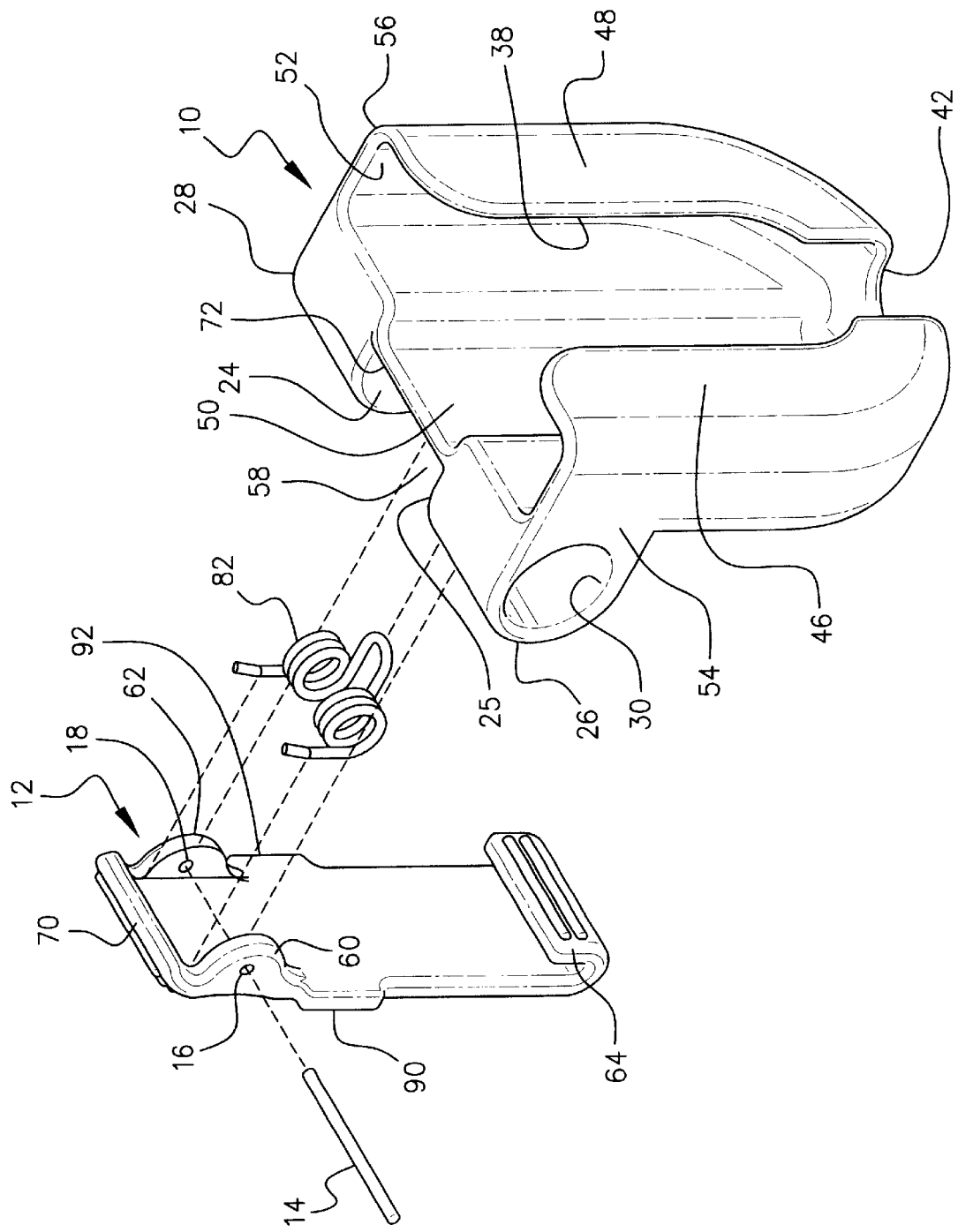
FIG. 1 is an exploded perspective view of the stethoscope holder and its belt mounting adapter.

Throughout the following detailed description, the same reference numerals refer to the same items in all figures. Referring to FIG. 1, the stethoscope holder housing 10 is rotatably attached to a belt adapter 12 by a longitudinal pin 14 axially aligned with bores 16 and 18, respectively in the belt adapter 12 and channels 20 and 22 found in the outer walls 24 and 25 of each ear piece receptacles 26 and 28. The ends of longitudinal pin 14 are press fit within channels 20 and 22, respectively. As shown in FIG. 1, receptacle 26 has an opening 30 for receipt of a stethoscope ear piece 32. In like manner, receptacle 28 has an opening 34 for receipt of stethoscope ear piece 36.

The stethoscope holder 10 has a front slot 38 for receipt of a stethoscope chest piece 40. A bottom of slot 38 has an opening 42 for receipt of a stethoscope tube 44. First and second front walls 46 and 48, respectfully are spaced apart to form the slot 38. In addition, front walls 46 and 48 are spaced apart from back wall 50 by side walls 54 and 56 to form receptacle 52 for the stethoscope chest piece 40. The ear piece receptacle 26 embodies a top portion of side wall 54 and ear piece receptacle 28 embodies a top portion of side wall 56.

The ear piece receptacles 26 and 28 project backwardly from back wall 50. Their opposed exterior walls 24 and 25 are spaced apart to form a channel 58 for receipt of a first and second upper side wall portions 60 and 62, respectively of the adapter 12. A U-shaped belt gripper 64 at the bottom of adapter 12 fits under the belt 66 of the car giver 68. A longitudinal top frame member 70 pivots towards the top edge 72 of the housing 10.

Figure 2:
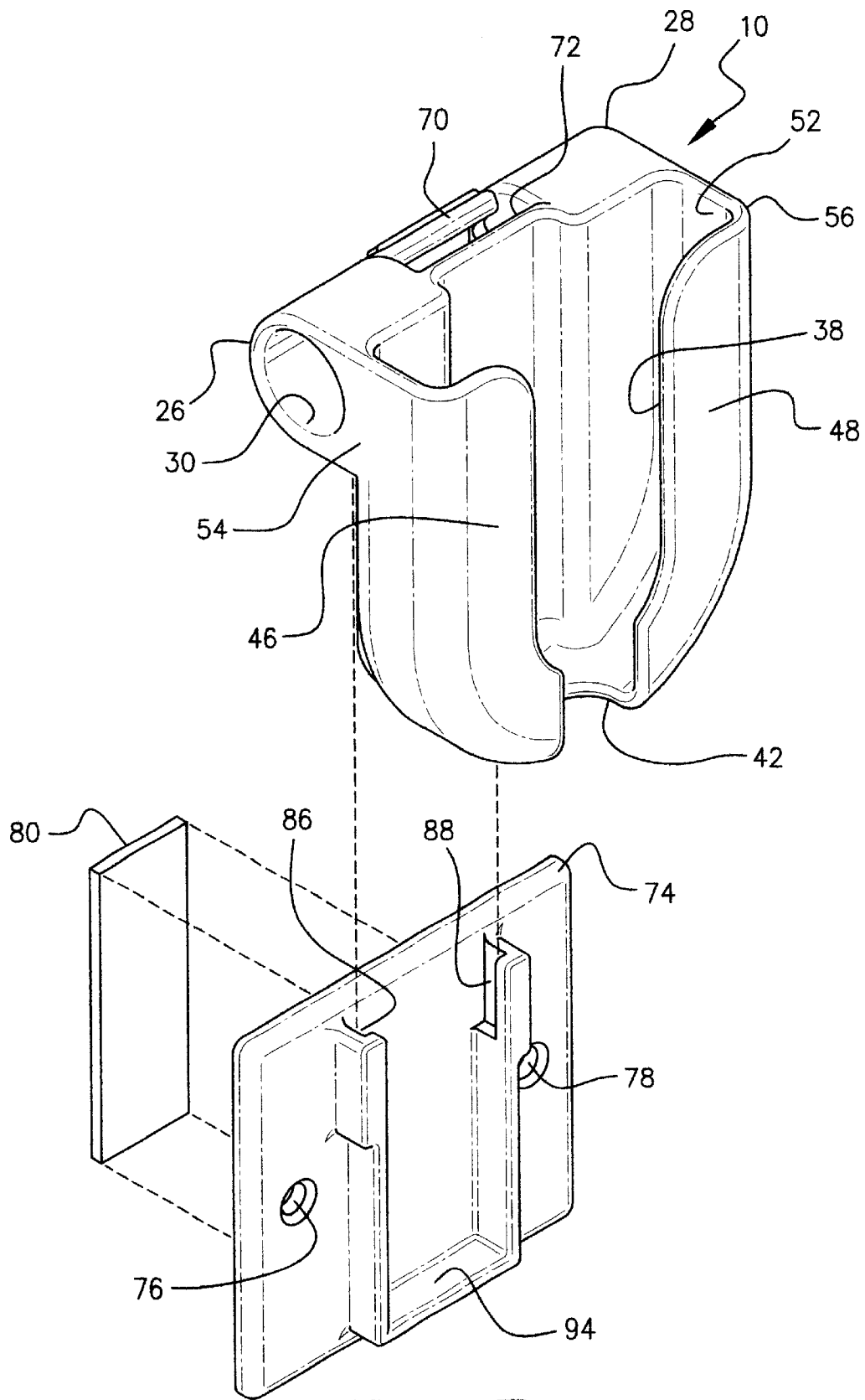
FIG. 2 is an exploded perspective view of the stethoscope holder and adapter with a wall mount.
Figure 3:
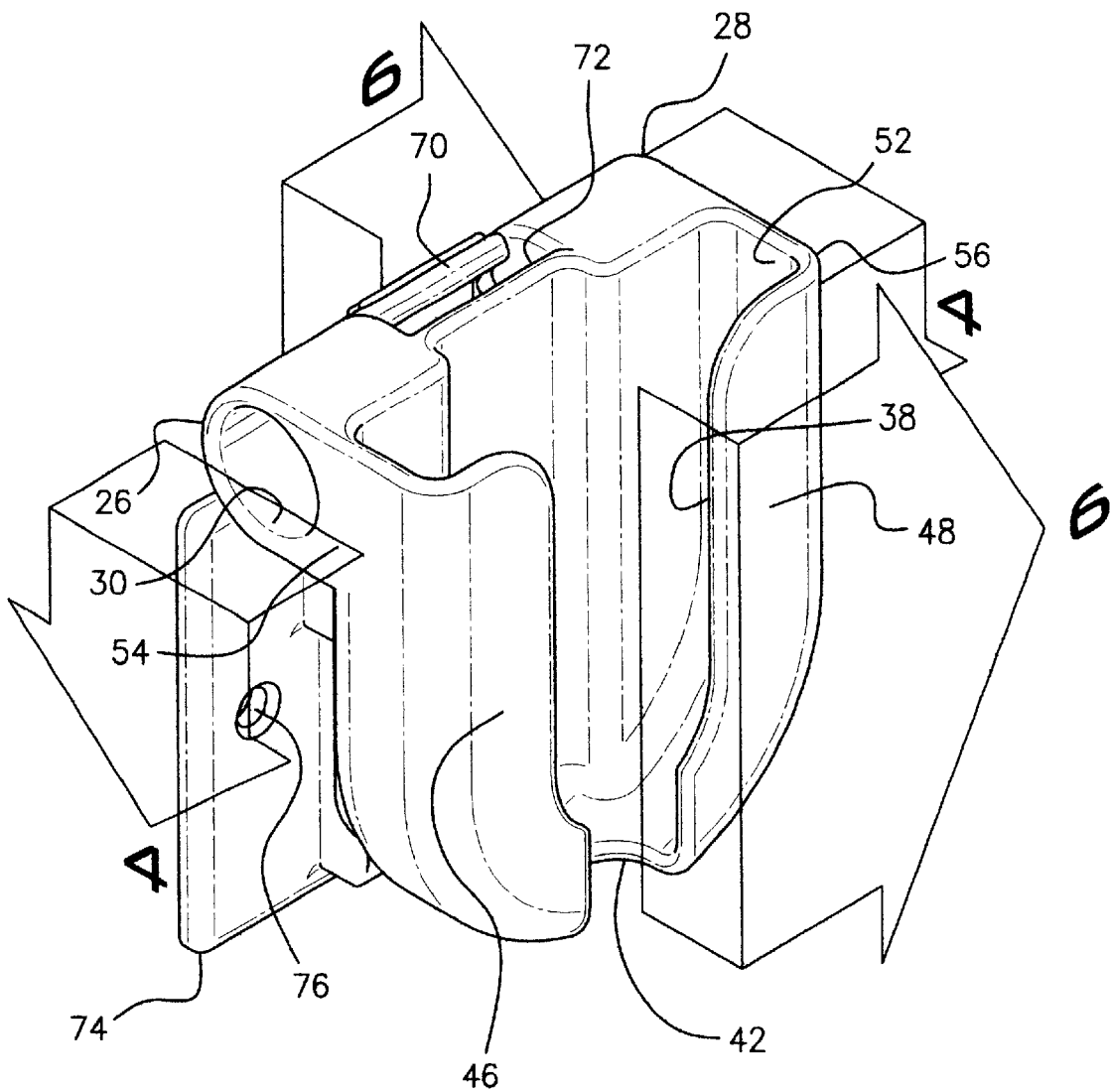
FIG. 3 is a perspective view of the stethoscope holder and attached belt mounting adapter resting in a wall mount.

When not in use, the stethoscope holder housing 10, together with belt adapter 12 can be stored on a wall bracket 74 as shown in FIG. 2. The wall bracket 74 can be mounted with screws (not shown) through bores 76 and 78 or with double sided sticky tape 80 to a wall. Slots 86 and 88 in wall bracket 74 receive side ears 90 and 92 of the adapter 12 with the gripper 64 resting on shelf 94 to retain the combined adapter 12 and housing 10 on the wall bracket 74.

Figure 4:
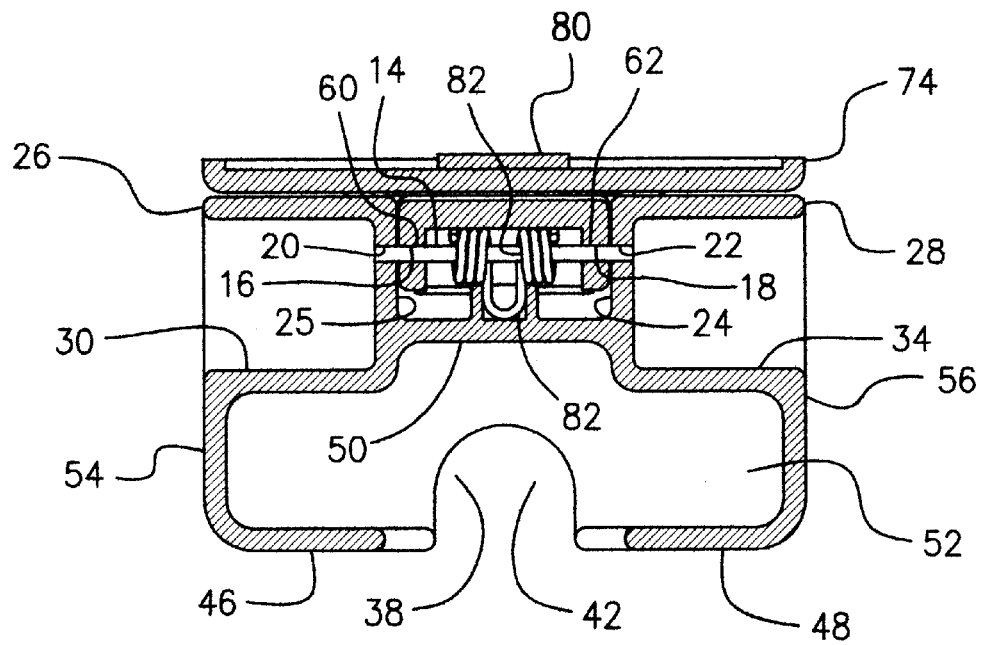
FIG. 4 is a cross sectional view along lines 4—4 in FIG. 3.
Figure 5:
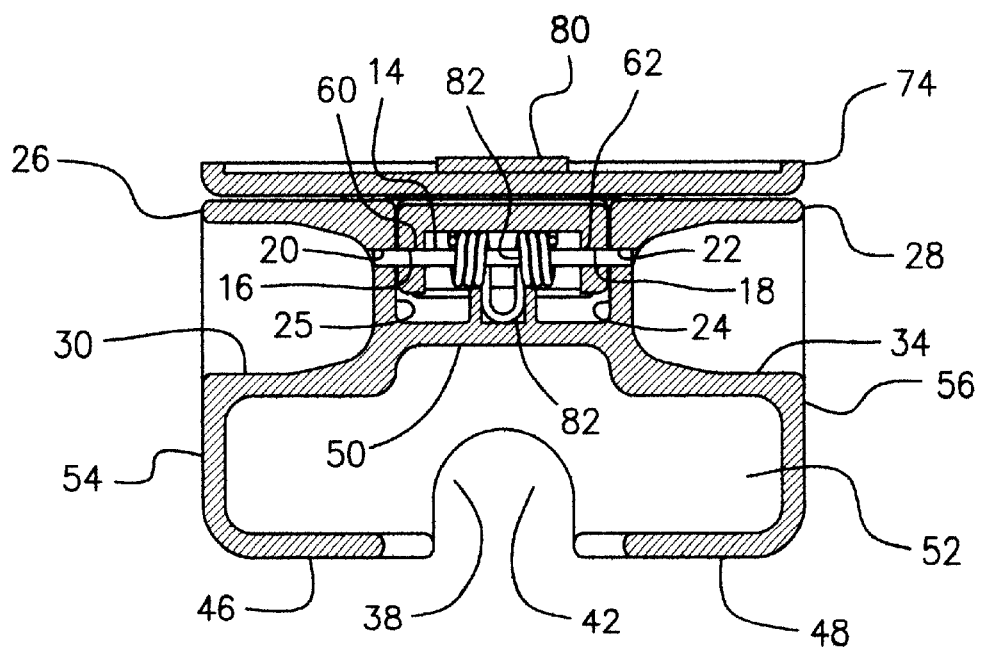
FIG. 5 is a cross sectional view similar to the FIG. 3 cross sectional view along lines 4—4, but with an alternate ear piece receptacle interior configuration.
Figure 6:
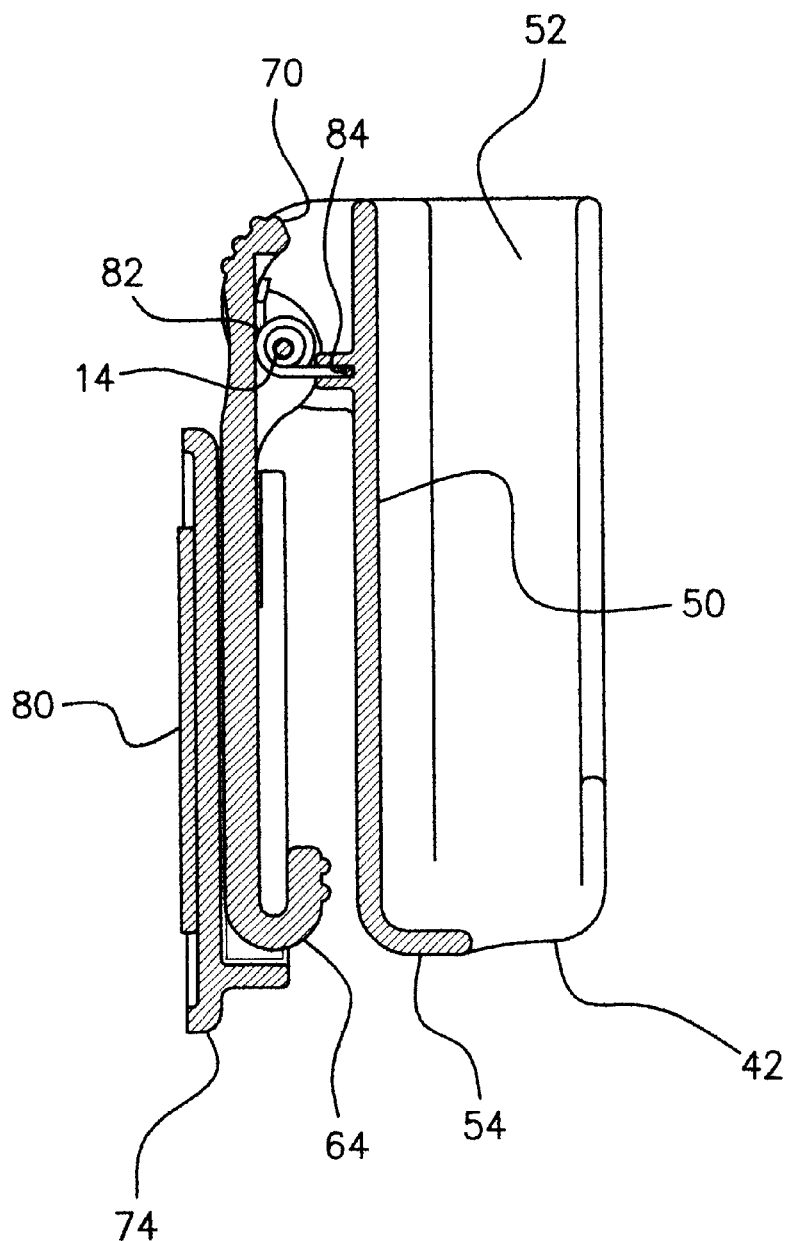
FIG. 6 is a cross sectional view along lines 6—6 in FIG. 3.
Figure 7:
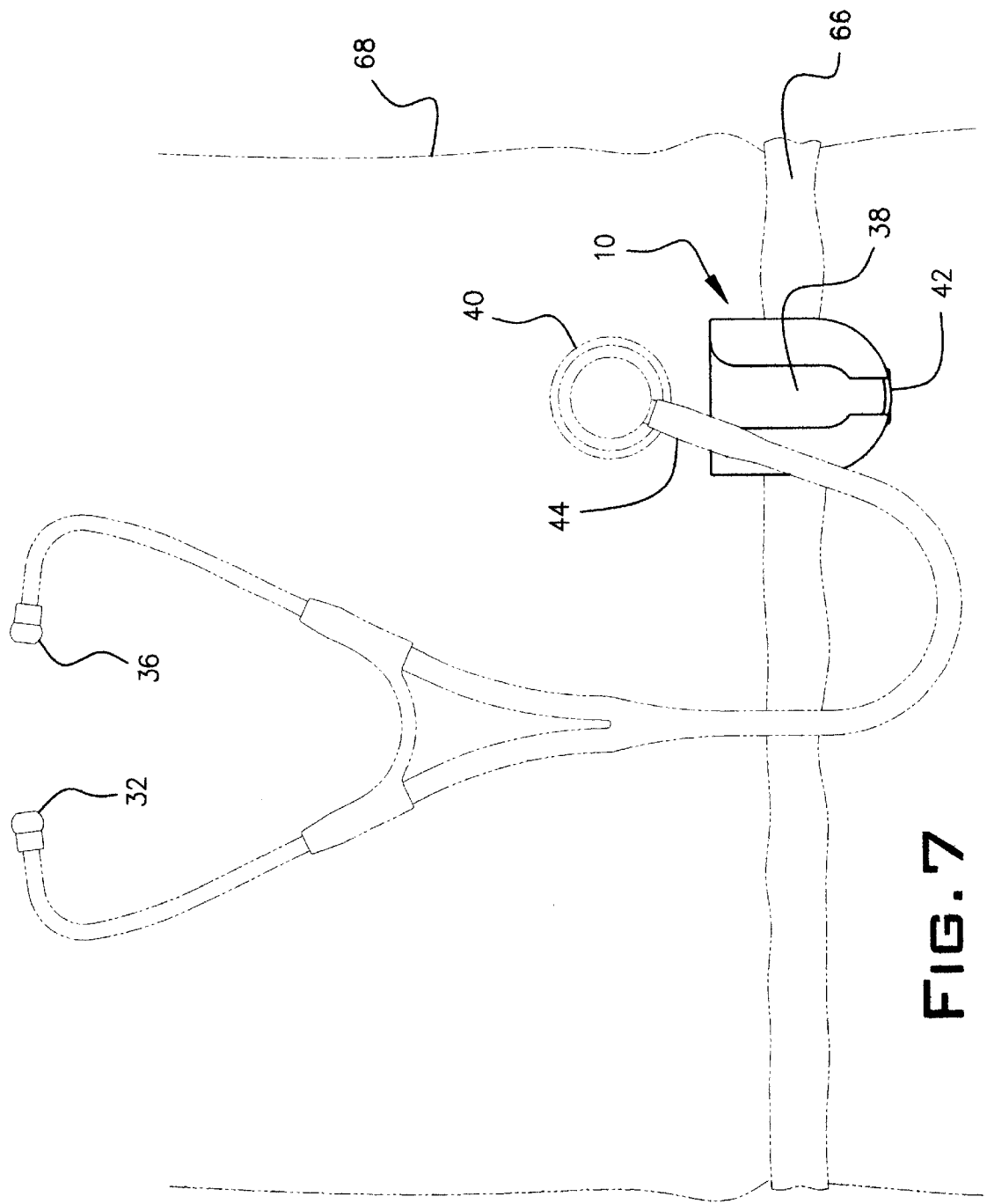
FIG. 7 is a front view of the stethoscope holder and belt adapter mounted on a care giver's belt.
Figure 8:
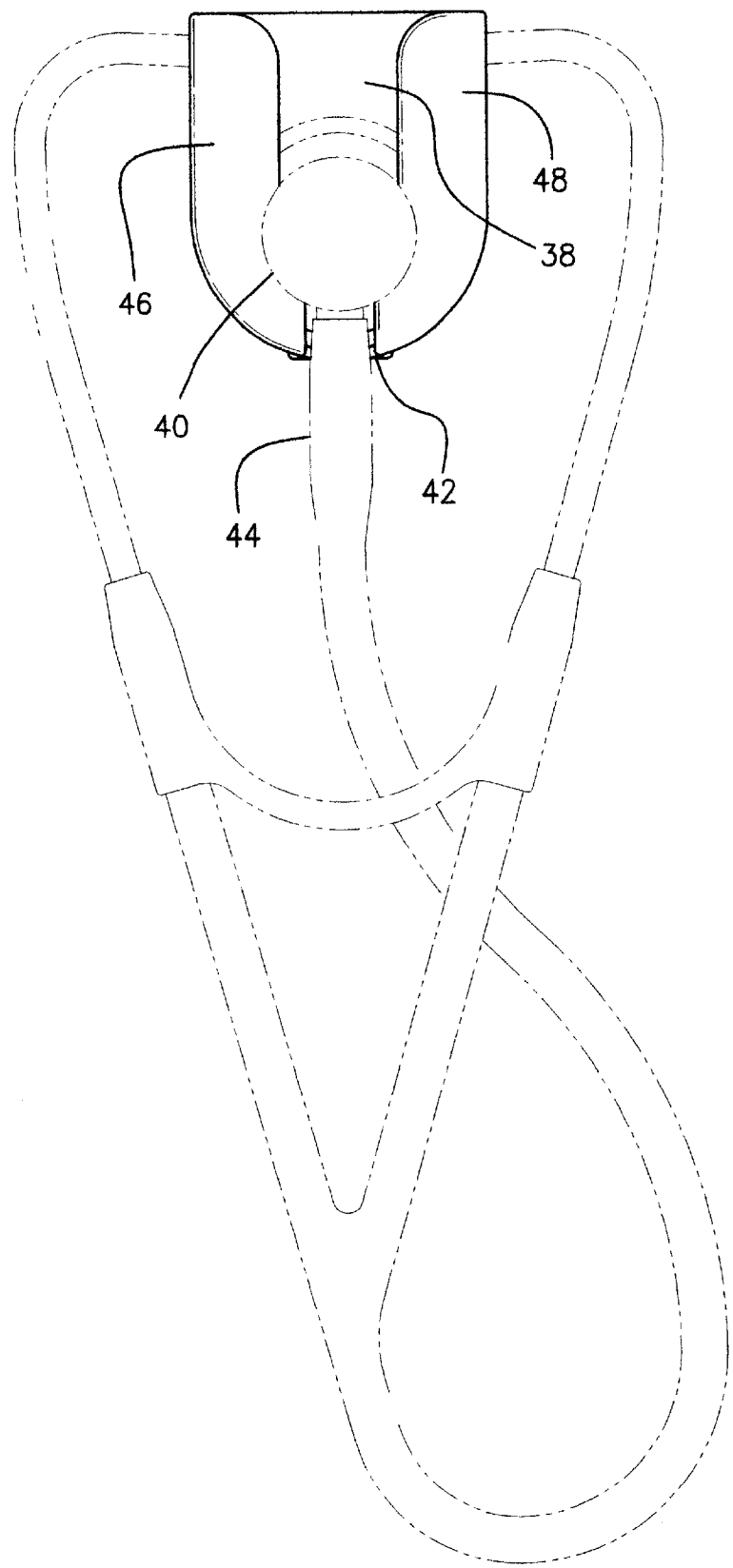
FIG. 8 is a front view of the stethoscope holder retaining the chest piece and ear pieces of a stethoscope.
Figure 9:
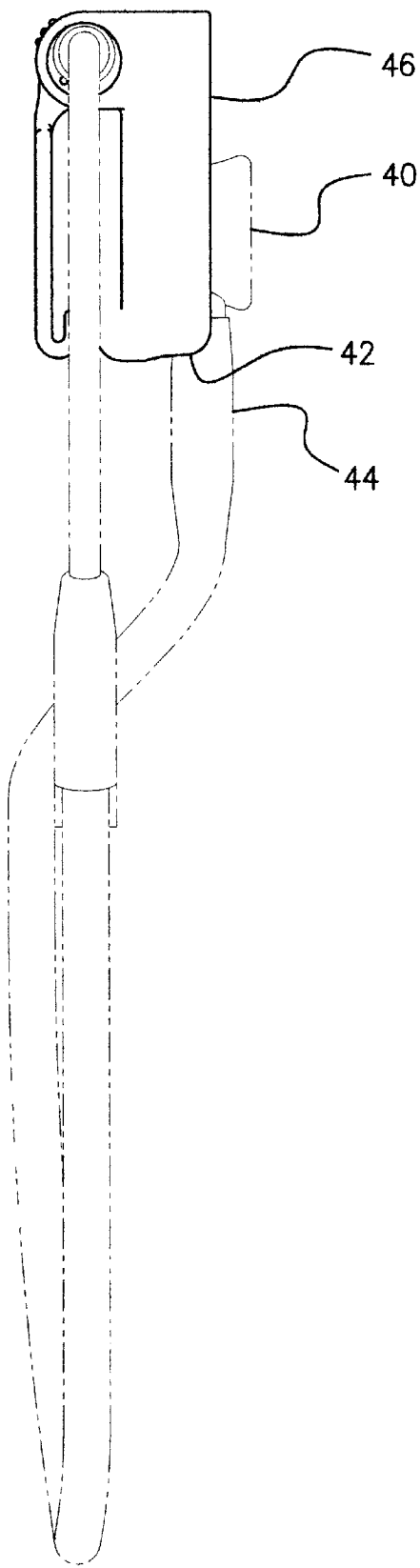
FIG. 9 is a side view of the stethoscope holder retaining the chest piece and ear pieces of a stethoscope.

Rod 14 as shown in FIGS. 4 and 5 passes through spring 82 to maintain the adapter 12 in an upright position against the belt 66 of the care giver 68. A terminal end 84 of spring 82 is embedded in back wall 50 of the stethoscope holder housing 10.

The housing 10 and adapter 12 can be made out of any common high strength plastic with each component 10 and 12 separately molded. The rod or longitudinal pin 14 and spring 82 can be made out of steel.

The above description has described specific structural details of the combined belt adapter and stethoscope holder housing of this invention. However, it will be within the knowledge of one having ordinary skill in the art to make modifications without departing from the spirit and scope of the underlying invention's inventive concept. The inventive concept is not limited to the structure described, but includes such modifications as would be considered equivalent.

Having thus described the invention what is claimed and desired to be secured by letters patent is:

1. A stethoscope holder with combined belt adapter for supporting a stethoscope, the stethoscope holder and combined belt adapter comprising:

an integral stethoscope holder housing having a back wall, first and second side walls, an upper portion of each side wall having a stethoscope ear piece receptacle, a pair of front walls spaced apart to form a slot therebetween, the pair of front walls spaced apart from the back wall to form an opening for receipt of a stethoscope chest piece, an opening at the bottom of the slot for receipt of a stethoscope tube; and the belt adapter adapted for mounting on a belt of a care giver, the adapter hingedly attached to the stethoscope holder housing by a rod axially aligned with bores in an inner wall of each ear piece receptacle and a bore in parallel upper side wall portions of the adapter, so that with the adapter mounted, the stethoscope chest piece rests in the opening inside the slot, each stethoscope ear piece rests in an ear piece receptacle and the stethoscope tube descends through the opening at the bottom of the slot in the housing.

2. The stethoscope holder housing with combined belt adapter according to claim 1 wherein a wall bracket has a pair of slots to receive a corresponding pair of side projecting ears on the belt adapter and a shelf to receive a U-shaped belt gripper positioned on a bottom portion of the adapter, to store the stethoscope holder and belt adapter when not in use on the care giver.

3. The stethoscope holder housing with combined belt adapter according to claim 1 wherein a spring is mounted over the rod and a terminal end of the spring is embedded in the back wall of the holder housing.

4. The stethoscope holder housing with combined belt adapter according to claim 1 wherein each end of the rod is press fit into the inner wall of each ear piece receptacle.

5. The stethoscope holder housing with combined belt adapter according to claim 1 wherein an opposed exterior wall of each ear piece receptacle is spaced apart for receipt of a first and second upper side wall portion of the adapter.

6. The stethoscope holder housing with combined belt adapter according to claim 1 wherein the holder housing and belt adapter are molded from a plastic.

* * * * *